United States Patent [19]

Beard et al.

[11] Patent Number: 5,368,021

[45] Date of Patent: Nov. 29, 1994

[54] SYSTEM FOR HANDLING AND MONITORING RESPIRATORY WASTE STREAMS

[75] Inventors: Lane F. Beard, Waukesha; Daniel I. Disch, Beaver Dam; John G. Storch, Wauwatosa, all of Wis.

[73] Assignee: Criticare Systems, Inc., Waukesha, Wis.

[21] Appl. No.: 865,978

[22] Filed: Apr. 9, 1992

[51] Int. Cl.$^5$ .................. A62B 7/10; A62B 19/00; A62B 83/02; B01D 53/22

[52] U.S. Cl. .................. 128/205.12; 128/205.27; 128/205.29; 128/912; 73/863.23; 96/4

[58] Field of Search .............. 128/716, 719, 730, 729, 128/205.12, 205.23, 205.27, 205.29, 912; 55/270, 274, 350, 158, 215; 73/863.23; 604/317–320, 322

[56] References Cited

U.S. PATENT DOCUMENTS

| | | | |
|---|---|---|---|
| 3,523,408 | 8/1970 | Rosenberg | 55/318 |
| 3,719,197 | 3/1973 | Pannier, Jr. et al. | 137/205 |
| 3,751,879 | 8/1973 | Allington | 55/158 |
| 3,782,083 | 1/1974 | Rosenberg | 55/491 |
| 3,803,810 | 4/1974 | Rosenberg | 55/159 |
| 3,858,573 | 1/1975 | Ryan et al. | 73/421.5 R |
| 3,976,450 | 8/1976 | Marcote et al. | 55/158 |
| 4,034,578 | 12/1981 | Hakala et al. | 55/189 |
| 4,092,137 | 5/1978 | Howe et al. | 55/337 |
| 4,167,667 | 9/1979 | Hall et al. | 250/288 |
| 4,187,390 | 2/1980 | Gore | 174/102 R |
| 4,190,426 | 2/1980 | Ruschke | 55/185 |
| 4,197,858 | 4/1980 | Osborn | 128/718 |
| 4,232,683 | 11/1980 | Bartholomew et al. | 128/725 |
| 4,270,564 | 6/1981 | Blackburn et al. | 137/240 |
| 4,298,358 | 11/1981 | Ruschke | 55/185 |
| 4,327,718 | 5/1982 | Cronenberg | 128/205.12 |
| 4,360,018 | 11/1982 | Choksi | 128/205.12 |
| 4,382,806 | 5/1983 | Hakala et al. | 55/18 |
| 4,440,177 | 4/1984 | Anderson et al. | 128/719 |
| 4,445,012 | 4/1984 | Blackbürn et al. | 200/61.05 |
| 4,446,869 | 5/1984 | Knodle | 128/716 |
| 4,456,014 | 6/1984 | Buck et al. | 128/719 |
| 4,459,139 | 7/1984 | vonReis et al. | 55/189 |
| 4,465,485 | 8/1984 | Kashmer et al. | 604/320 |
| 4,476,708 | 10/1984 | Baker et al. | 73/23 |
| 4,546,778 | 10/1985 | Sullivan | 128/718 |
| 4,549,553 | 10/1985 | Hochberg | 128/719 |
| 4,558,708 | 12/1985 | Labuda et al. | 128/719 |
| 4,572,208 | 2/1986 | Cutler et al. | 128/718 |
| 4,579,568 | 4/1986 | Ricciardelli et al. | 155/189 |
| 4,592,368 | 6/1986 | Ricciärdelli et al. | 128/719 |
| 4,600,412 | 7/1986 | Liston et al. | 55/189 |
| 4,619,269 | 10/1986 | Cutler et al. | 128/719 |
| 4,668,257 | 5/1987 | van der Meer et al. | 55/267 |
| 4,678,488 | 7/1987 | Howard et al. | 55/406 |

(List continued on next page.)

OTHER PUBLICATIONS

Capnomac II Airway Monitor, Operator's Manual, Feb. 1990, pp. sections 6.2–6.2.3, 6.3–6.4, 6.6.

Criticare Systems, Inc. Proprietary Information, Mar. 1991.

*Primary Examiner*—Kimberly L. Asher
*Attorney, Agent, or Firm*—Reinhart, Boerner, Van Deuren, Norris & Rieselbach

[57] ABSTRACT

A system for handling and disposing of respiratory waste from a patient's respiratory circuit. The system includes a device for providing an inhalable input fluid containing a gas to the patient's respiratory circuit, a device for providing an output path for the expired respiratory waste, a device for filtering and handling the respiratory waste with a filter portion including (a) an input port on a first side of a filter media for separating a gas from liquids and solids, (b) a first chamber on the first side, (c) a first output port for liquids and solids on the first side, (d) a second side of the filter media having a second chamber and (e) a second output port on the second side of the filter media for the gas with the first chamber geometry enabling preferential removal of any solids occluding the filter media preventing gas flow to the second chamber.

21 Claims, 2 Drawing Sheets

U.S. PATENT DOCUMENTS

| | | | |
|---|---|---|---|
| 4,717,403 | 1/1988 | Choksi | 55/429 |
| 4,727,871 | 3/1988 | Smargiassi et al. | 128/204.17 |
| 4,798,229 | 1/1989 | Rantala | 138/42 |
| 4,799,374 | 1/1989 | Bossart et al. | 128/719 |
| 4,805,611 | 2/1989 | Hodgkins | 128/207.14 |
| 4,821,737 | 4/1989 | Nelson | 128/730 |
| 4,856,531 | 8/1989 | Meriläninen | 128/719 |
| 4,867,153 | 9/1989 | Lorenzen et al. | 128/205.12 |
| 4,870,961 | 10/1989 | Barnard | 128/202.27 |
| 4,883,353 | 11/1989 | Hausman et al. | 356/41 |
| 4,886,528 | 12/1989 | Aantonen et al. | 55/158 |
| 4,921,642 | 5/1990 | LaTorraca | 261/142 |
| 4,924,860 | 5/1990 | Larsen et al. | 128/205.12 |
| 4,957,629 | 5/1990 | Smith et al. | 210/443 |
| 4,985,055 | 1/1991 | Thorne et al. | 55/189 |
| 4,997,463 | 3/1991 | Ricciardelli | 55/165 |
| 5,009,682 | 4/1991 | Hagelauer | 55/159 |
| 5,025,806 | 6/1991 | Palmer et al. | 128/203.12 |
| 5,026,407 | 6/1991 | Tobey | 55/185 |
| 5,045,077 | 9/1991 | Blake, III | 604/321 |
| 5,046,491 | 9/1991 | Derrick | 128/200.24 |
| 5,070,245 | 12/1991 | Rantala et al. | 250/343 |
| 5,072,737 | 12/1991 | Goulding | 128/718 |

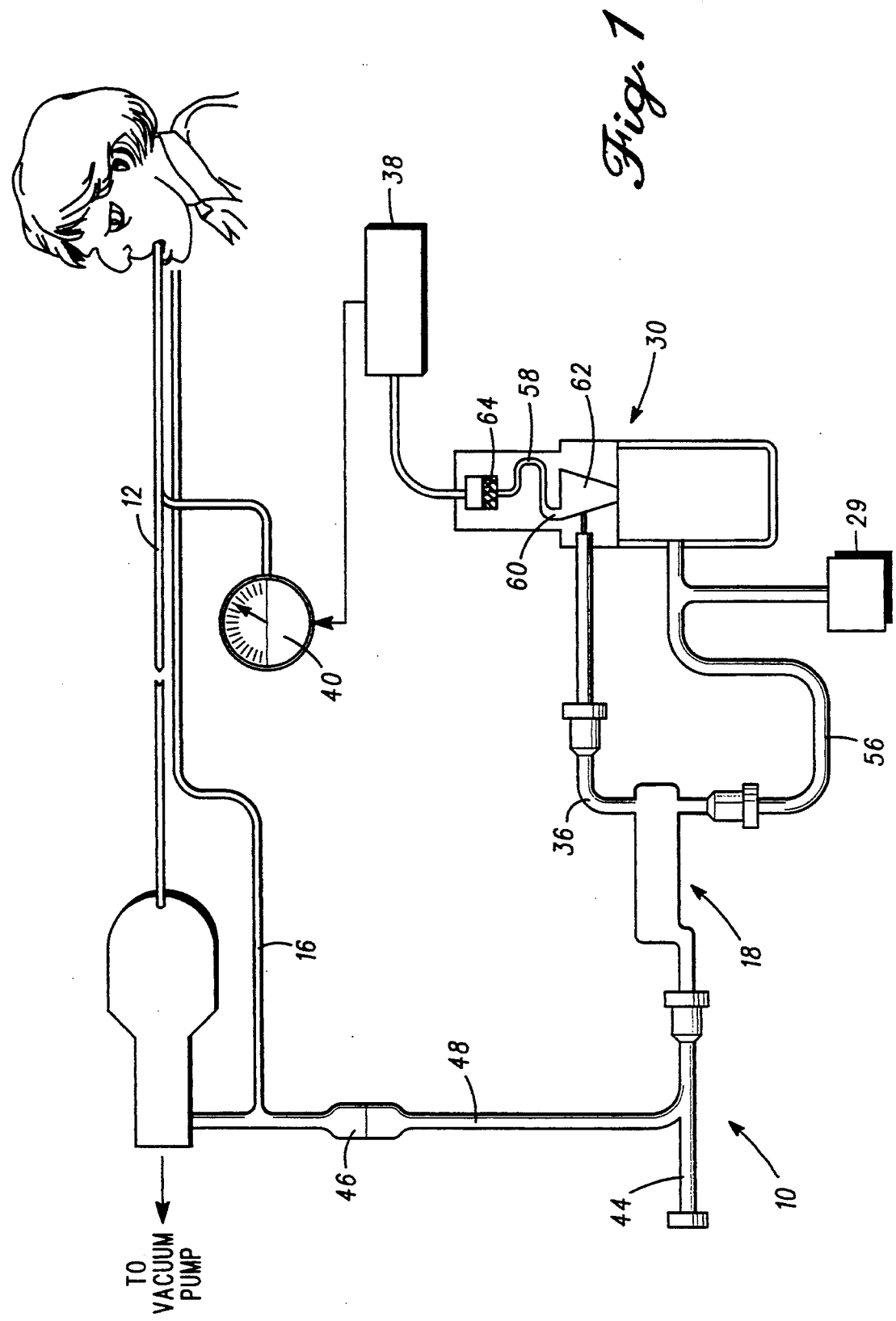

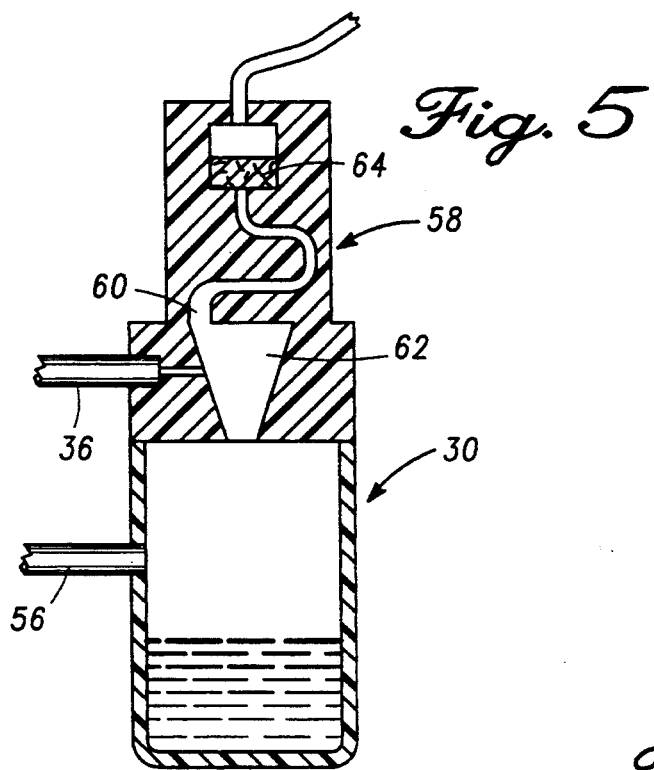
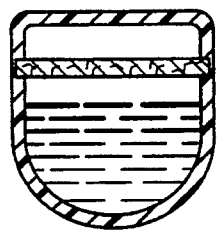
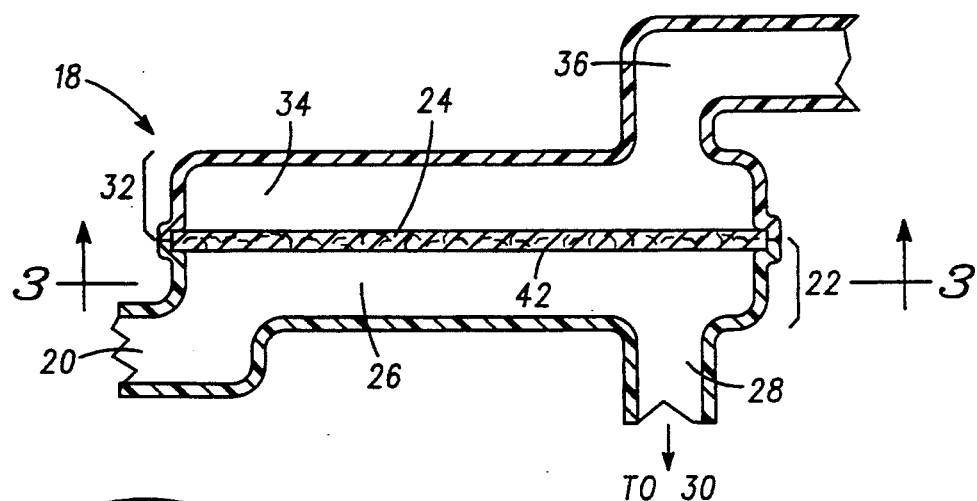
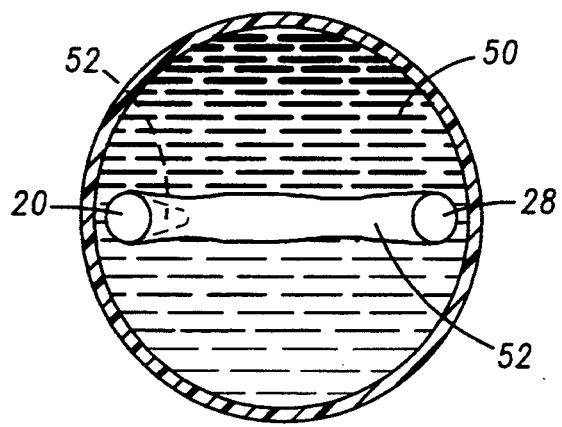

SYSTEM FOR HANDLING AND MONITORING RESPIRATORY WASTE STREAMS

The present invention is generally concerned with sampling, handling and disposing of a respiratory waste stream of a patient under medical care. More particularly, the invention is concerned with a respiratory waste system for separating gas from liquids, solids and viscous fluids in a patient's respiratory waste stream.

During and after surgical procedures it is important to monitor and/or control a patient's respiratory circuit to insure optimum recovery conditions for the patient. Numerous systems exist to carry out such functionalities, but all such systems suffer from frequent stoppage arising primarily from clogging of the system by mucous, blood and other materials secreted by the patient's respiratory system arising from surgery or from other trauma to the patient's respiratory circuit. Some attempts to alleviate this problem have involved usage of complex, dedicated systems which suffer from the disadvantage that the system must be disinfected after each patient usage. Other attempted solutions involve using disposable components which results in the need to make very frequent changes of the disposable components which are easily clogged by a patient's respiratory waste. These forms of disposable components necessitate frequent manual labor intervention and stoppage of the system monitoring and/or controlling the patient's respiratory circuit.

It is therefore an object of the invention to provide an improved method and apparatus for monitoring and/or controlling a patient's respiratory circuit.

It is another object of the invention to provide a novel system for handling and disposing of the respiratory waste of a patient.

It is a further object of the invention to provide an improved system and method for filtering gas from liquids, solids and viscous fluids in a patient's expired respiratory stream.

It is an additional object of the invention to provide a novel filter device having a design enabling removal of solids or viscous fluids occluding the filter media.

It is yet another object of the invention to provide an improved system and method for filtering an expired respiratory stream and trapping liquids, solids or viscous fluids present in the expired respiratory stream.

Various features of the invention are set forth in the drawings described herein below wherein like elements have like numerals throughout the drawings.

DESCRIPTION OF THE DRAWINGS

FIG. 1 illustrates a system for monitoring and/or handling a patient's expired respiratory stream;

FIG. 2 depicts a filter portion of the system shown in FIG. 1;

FIG. 3 illustrates a cross section taken along line 3—3 in FIG. 2;

FIG. 4 depicts a prior art filter element in a system for monitoring and/or handling a patient's respiratory circuit; and FIG. 5 shows an enlarged view of the trap device component shown in FIG. 1.

Other objects and advantages of the invention are included in the following detailed description and claims set forth thereafter.

DETAILED DESCRIPTION OF PREFERRED EMBODIMENTS

A system for monitoring and/or handling an expired respiratory stream of a patient is shown generally at 10 in FIG. 1. The system 10 can include means for providing input fluid to a patient's respiratory circuit or system. Such means can be, for example, an endotracheal tube 12 disposed in the patient's airway. Although the endotracheal tube 12 is illustrated as the preferred patient attachment, those of skill in the art would recognize that other conventional attachments, such as a cannula and face mask, may also be used. A means for providing an output path for expired respiratory waste can be, for example, the endotracheal tube 12 serving both input and output functions or a separate tube 16 can be provided. Other conventional arrangements can also be used to effectuate the input and output functions described above.

Means for filtering and handling the expired respiratory waste can be, for example, a filter housing 18 shown generally in FIG. 1 and in detail in FIG. 2. The filter housing 18 includes an input port 20 on a first side 22 of a filter media 24. An example of such a filter media 24 is a porous membrane (e.g., a FILTERTEK Corporation (a Wisconsin company) part number 63160 PTFE filter in a housing) having a pore size of approximately 0.1 to 1.0 microns, although the pore size is not critical to the invention. The filter media 24 functions to allow passage of gas only, being impervious to flow of fluids and solids. Therefore, the filter 18 causes the fluids and solids input through the input port 20 to pass through a first chamber 26 to a first output port 28. These fluids and/or solids are output to a trap device 30 to be described in more detail hereinafter.

The gas in the expired respiratory stream is passed through the filter media 24 into a second side 32 having a second chamber 34. A second output port 36 receives the gas and transfers the gas to an analytical unit 38 for analysis. The system 10 can function to modify the fluid input by a gas system 40 to the patient, responsive to the analysis of the expired respiratory stream. The input fluid can include, for example, humidified oxygen and/or oxygen/nitrogen, an anesthetic gas and a gas containing a drug for medical treatment of the patient.

The filter housing 18 further includes a construction of the first side 22 which enables preferential removal of solids and viscous fluids occluding first surface 42 of the filter media 24. During monitoring and handling of the patient's expired respiratory stream, significant quantities of mucous, blood and other waste secretions are carried into the respiratory stream. Such waste products eventually lead to occlusion or clogging of the filter media 24, blocking flow of the gas through the filter media 24. The system can be reactivated by input of fluid, such as water under pressure, into injection port 44 or by removal of fittings 46 and input into line 48.

The injected fluid enters into the first chamber 26 of the filter housing 18 by passing through the input port 20. The first chamber 26 has a passageway geometry enabling the pressurized input liquids to preferentially flow across the first surface 42 through at least part of the solids and/or viscous fluids 50 occluding the filter media 24 (see cleared path 52 in FIG. 3). The solids and/or viscous liquids 50 removed are forced to flow out the first output port 28 to the trap device 30. Therefore, the passageway geometry includes the first chamber 26 having an opening which is a disk type shape and having one dimension, such as the thickness perpendicular to the filter media 24, substantially less than the other two dimensions of the first chamber 26. In other forms of the invention the first chamber 26 can include a restrictive channel opening, such as a nozzle shape or restrictive opening 52 (in phantom in FIG. 3), to cause the preferential flow of the injected fluid enabling removal of the occluding solids and/or viscous fluids from the first surface 42.

The waste solids, fluids and viscous liquids removed by the injected fluid are output from the first output port 28 through output line 56 to the trap device 30 the solids, fluids and viscous liquids can be sampled as shown in FIG. 1 and analysis performed by device 29. Operation and use of this trap device 30 is explained in U.S. Pat. No. 4,924,860 which is incorporated by reference herein. An improvement over the invention described in the '860 patent includes a baffle 58 (see FIG. 5) disposed in conduit 60 between separation chamber 62 and sealing filter 64. The baffle 58 prevents inadvertent splashing of the sealing filter 64 which seals upon exposure to sufficient moisture levels indicative of a full water trap.

The system 10 exhibits substantial performance advantages over prior art systems and Table I below illustrates the lifetime for filter devices of the invention compared to currently used prior art devices of the applicant having an operating lifetime of less than about one case hour.

TABLE 1

Comparison of Case Hour Operation of Prior Art Filter System to Invention Filter Operation Performance A. A humidified operating room environment using prior art filter device:

| Number of samples: | 12 | | | | |
|---|---|---|---|---|---|
| Mean Lifetime: | 0.64 ± .46 case hours | | | | |
| Standard Deviations: | −2 | −1 | +1 | +2 | +3 |
| Number of Samples: | 0 | 8 | 2 | 1 | 1 |

B. A humidified operating room environment using Applicants' filter device:

| Number of samples: | 28 | | | | |
|---|---|---|---|---|---|
| Mean Lifetime: | 57.4 ± 27.7 case hours | | | | |
| Standard Deviations: | −3 | −2 | −1 | +1 | +2 |
| Number of Samples: | 1 | 3 | 6 | 13 | 5 |

(This data is believed to include as many as four units which are without the Applicants' Filter invention and explains some of the data at low performance levels.)

C. Using Applicants' filter device in an intensive care unit environment including humidification and normally producing mucous output from the patient.

| Number of samples: | 37 | | | |
|---|---|---|---|---|
| Mean Lifetime: | 84.3 ± 72 continuous hours | | | |
| Standard Deviations: | −2 | −1 | +1 | +2 |
| Number of Samples: | 13 | 2 | 14 | 8 |

While preferred embodiments of the invention have been shown and described, it will be clear to those skilled in the art that various changes and modifications can be made without departing from the invention in its broader aspects as set forth in the claims provided hereinafter.

We claim:

1. A system for handling and disposing of respiratory waste expired by a patient from a patient's respiratory circuit, comprising:

means for providing inhalable input fluid containing a gas to a patient's respiratory circuit;

means for providing an output path for expired respiratory waste from the patient's respiratory circuit;

means for filtering and handling the expired respiratory waste coupled to said means for providing an output path for the expired respiratory waste, said filtering and handling means comprising:

(a) a filter housing containing a first chamber and a filter media and also including an input port directing the expired respiratory waste into said first chamber on a first side of said filter media in the filter housing, said filter media separating gas from liquids, solids and viscous fluids in the expired respiratory waste and said filter media accumulating retained solids and viscous fluids;

(b) a first output port receiving said liquids, solids and viscous fluids input into said first chamber and retained by said filter media in the filter housing;

(c) a second side of said filter media in the filter housing having a second chamber; and (d) a second output port on said second side of said filter media in the filter housing outputting said gas through said filter media;

said first chamber of the filter housing having means for removing liquids, solids and viscous fluids which eventually occlude the first side of said filter media, said means for removing comprising said first chamber having a specific passageway geometry, and an injection port means for receiving pressurized liquid, said passageway geometry causing preferential flow of injected pressurized liquid into said input port, across the surface of said filter media and through at least a portion of said retained solids and viscous fluids occluding said filter media and removing at least part of said occluding solids and viscous fluids, said pressurized liquid and passageway geometry forcing said occluding solids and viscous fluids to flow out through said first output port.

2. The system as defined in claim 1 wherein said inhalable input fluid comprises a humidified gas.

3. The system as defined in claim 1 wherein said injected pressurized liquid comprises water.

4. The system as defined in claim 1 wherein said passageway geometry comprises an opening having one dimension substantially less than the other two dimensions characterizing said passageway.

5. The system as defined in claim 1 wherein said passageway comprises a disk shaped opening adjacent said filter media.

6. The system as defined in claim 5 wherein said disk has a thickness of less than about ten percent of the diameter of said disk.

7. The system as defined in claim 1 wherein said passageway geometry comprises a restrictive channel opening disposed within said first chamber.

8. The system as defined in claim 1 further including means coupled to said filtering means for trapping at least one of liquids, solids or viscous fluids received through said first output port.

9. A system for handling and disposing of respiratory waste expired from a respiratory circuit of a patient, comprising:

means for providing an output path for expired respiratory waste from a respiratory circuit of a patient;

means for filtering and handling the expired respiratory waste coupled to said means for providing an output path for filtering and handling, said means comprising:

(a) means for separating a gas from liquids, solids and viscous fluids in the expired respiratory waste, including:
  (1) a filter housing having a first open chamber and containing a filter media, said filter housing having a first side and also including an input port directing expired respiratory waste into said first open chamber on said first side of said filter media, said filter media separating the gas from the liquids, solids and viscous fluids;
  (2) a first output port receiving the liquids, solids and viscous fluids passed through said first open chamber on said first side of said filter media;
  (3) a second side of said filter media having a second open chamber; and
  (4) a second output port on said second side of said filter media outputting said gas passed through said filter media; and
(b) an injection port means for inputting pressurized fluid into said means for filtering and handling, means for causing preferential flow through at least part of solids and viscous fluids retained by said filtering and handling means during use of the system, said means for causing preferential flow forcing the pressurized fluid and at least part of the retained solids and viscous fluids to flow out through said first output port; and
said means for causing preferential flow includes said filter housing having a passageway geometry which comprises an opening having one dimension substantially less than the other two dimensions characterizing said passageway geometry.

10. The system as defined in claim 9 further including means for providing gas containing inhalable input fluid to the respiratory circuit of a patient, said gas containing inhalable input fluid being at least one of humidified gas, an anesthetic containing gas and a gas containing a treatment drug.

11. The system as defined in claim 9 further including means coupled to said filtering and handling means for trapping liquids, solids, and viscous fluids passing through said output port.

12. The system as defined in claim 9 wherein said means for separating gas from liquids, solids and viscous fluids comprises a gas/liquid filter barrier.

13. The system as defined in claim 9 wherein said means for causing preferential flow comprises a narrow passageway between the opening to said filtering and handling means and said first output port.

14. The system as defined in claim 9 wherein said passageway geometry comprises a disk shape.

15. A device for filtering liquids, solids and viscous fluids from a respiratory waste stream expired from a patient's respiratory circuit, comprising:
  a filter housing including a filter media and an input port directing the expired respiratory waste into the filter housing on a first side of said filter media, said filter media separating gas from liquids, solids and viscous fluids, accumulating retained solids and viscous fluids, and becoming occluded dung use of the device;
  a first chamber in the filter housing on said first side of said filter media;
  a first output port on the filter housing receiving said liquids, solids and viscous fluids passing through said first chamber of said first side of said filter media;
  a second side of said filter media in the filter housing having a second open chamber; and
  a second output port on the filter housing opening from said second side of said filter media receiving said gas passed through said filter media, an injection port means for receiving pressurized liquid, said first chamber having a geometry forcing said pressurized liquid which has been injected into said filter housing to preferentially flow into said input port across at least part of the surface of said filter media and through said retained solids and viscous fluids occluding said filter media, said pressurized liquid injected into said filter housing clearing and carrying therewith the pressurized liquid, said retained solids and viscous fluids occluding said filter media out said first output port.

16. The device as defined in claim 15 wherein said filter media is impervious to liquids, solids and viscous liquids while allowing passage of gases.

17. The device as defined in claim 15 further including means coupled to said device for trapping liquids, solids or viscous fluids received from said first output port of said filter housing.

18. A system for analyzing a gas exhaled from a patient's expired respiratory stream, comprising:
  means for providing an output path for the patient's expired respiratory stream which includes (1) a gas and (2) liquids, solids and viscous fluids;
  means coupled to said output path means for sampling at least part of the patient's expired respiratory stream and including means for filtering and handling the patient's expired respiratory stream, comprising:
  (a) a filter housing including a filter media for separating a sample of the gas from the liquids, solids and viscous fluids in the patient's expired respiratory stream and the filter housing including an input port opening to a first side of said filter media and said filter media accumulating on the first side solids and viscous fluids during use of said system;
  (b) a first chamber in the filter housing on said first side of said filter media;
  (c) a first output port on the filter housing on said first side of said filter media for receiving the liquids, solids and viscous fluids accumulated by said first side of said filter media;
  (d) a second side of said filter media in the filter housing, said second side having an associated second chamber; and
  (e) a second output port on said second side of said filter media for outputting the gas passed through said filter media;
  said first chamber including means for injecting pressurized liquids into said first chamber of the filter housing for causing preferential flow of the pressurized liquids into said input port to said first output port along a path in contact with a surface of said filter media in said first chamber of the filter housing and through at least part of said accumulated solids and viscous fluids occluding said filter media said pressurized liquid and accumulated solids and viscous fluids flowing out said first output port and clearing a flow path through said filter media to allow the gas to flow through said filter media to said second side of said filter media and into said second chamber and out said second output port at least part of the liquids, the retained solids and viscous fluids flowing out said first output port of the filter housing, said means for causing preferential flow of the pressurized liquids comprising the geometry of said first chamber forming a fluid flow path of least resistance along the surface of said filter media between said input port and said first output port; and means for performing analysis of the gas output from said second output port.

19. The system as defined in claim 18 further including means for performing analysis of a least part of the liquids and solids received from said first output port.

20. The system as defined in claim 18 wherein said passageway geometry comprises a substantially flat plate like opening.

21. A system for handling and disposing of respiratory waste expired by a patient from a patient's respiratory circuit, comprising:

means for providing an input and an output path for fluid flow to and from the patient's respiratory circuit;

means for filtering and handling the fluid flow;

means coupled to said means for filtering and handling for trapping at least one of liquids, solids and viscous fluids received from said filtering and handling means, said means for trapping including a separation chamber for holding the liquids, solids and viscous fluids and a water sensitive seal means for sealing said separation chamber when filled, and a baffle comprised of a non-straight line, angled pathway disposed between said separation chamber and said water sensitive seal means, said baffle preventing water agitation from said separation chamber from contacting said seal means and causing premature sealing by said seal means.

* * * * *